United States Patent [19]

Farnung

[11] Patent Number: 4,655,883
[45] Date of Patent: Apr. 7, 1987

[54] PROCESS FOR THE PREPARATION OF PHOSPHONIC ACID ESTERS

[75] Inventor: Winfried Farnung, Münster, Fed. Rep. of Germany

[73] Assignee: Hoechst Aktiengesellschaft, Frankfurt am Main, Fed. Rep. of Germany

[21] Appl. No.: 614,874

[22] Filed: May 29, 1984

[30] Foreign Application Priority Data

Jun. 1, 1983 [DE] Fed. Rep. of Germany ....... 3319795

[51] Int. Cl.[4] ............................................. C25C 1/00
[52] U.S. Cl. ................................ 204/59 F; 204/59 R
[58] Field of Search ............................ 204/59 R, 59 F

[56] References Cited

U.S. PATENT DOCUMENTS 4,124,456 11/1978 Yagupolsky et al. ............. 204/59 R
4,337,125 6/1982 Kuch et al. ....................... 204/59 R Primary Examiner—Andrews. R. L.
Attorney, Agent, or Firm—Curtis, Morris & Safford

[57] ABSTRACT

The present invention relates to a new process for the preparation of phosphonic acid esters of the formula I

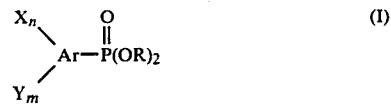

in which Ar denotes phenyl, a binuclear or polynuclear aromatic radical, cycloheptatrienyl, furyl or pyridyl, X denotes (substituted) alkyl, (substituted) alkoxy or optionally substituted aryl, aryloxy, heterocyclyloxy or arylmercapto radicals, phenylcarbonylamino, alkylcarbonylamino or alkoxycarbonylamino, alkylmercapto, alkoxycarbonyloxy, alkoxycarbonylalkoxy, phenylaminocarbonyloxy or alkylaminocarbonyloxy or two radicals X in the orthoposition together form a (substituted) ($C_3$–$C_4$) chain in which 2 carbon atoms can be replaced by oxygen, Y denotes halogen, alkoxycarbonyl, alkylcarbonyl, nitro, nitroso, cyano, alkylsulfonyl, phenylsulfonyl, alkoxysulfonyl, phenoxysulfonyl, alkoxy/alkylphosphinyl, halogenated alkyl, formyl or (substituted) amidosulfonyl, R denotes alkyl, n denotes 1, 2 or 3 and m denotes 0, 1, 2 or 3, wherein a compound of the formula II

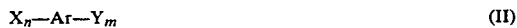

is subjected to anodic oxidation in the presence of a compound of the formula III

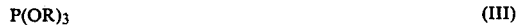

and of an alkanol in an undivided electrolytic cell. Some of the compounds obtainable by this process are new.

5 Claims, No Drawings

PROCESS FOR THE PREPARATION OF PHOSPHONIC ACID ESTERS

The present invention relates to an electrochemical process for the preparation of aromatic and heteroaromatic phosphonic acid esters.

The preparation of arylphosphonic acids by conventional processes of synthesis by the direct introduction of the phosphorus grouping without the use of electrochemical methods is known from Houben-Weyl, "Organische Phosphorverbindungen" ("Organic Phosphorus Compounds"), Volume XII/1, pages 338 et seq. (1963) and the supplementary volume "Phosphorverbindungen II" ("Phosphorus Compounds II"), E 2, pages 300 et seq. (1982).

These methods suffer, however, from disadvantages relating to industrial use, such as, for example, working with anhydrous solvents, removal of harmful substances produced as by-products, precursors which are difficult to obtain and unsatisfactory yields.

It is also known that aromatic compounds can be phosphonylated electrochemically with trialkyl phosphites (H. Ohmori, S. Nakai, M. Masui, J. C. S.; Perkin I 1979, 2023 and Chem. Pharm. Bull. 27, 1271 (1979)). The reactions are carried out under a controlled potential in a divided cell on glass-like carbon as the anode material. However, the electrochemical reaction only produces a trialkoxyarylphosphonium salt which then has to be reacted, in a second process stage, with sodium iodide in acetone to give the phosphonic acid ester.

Because of the importance of arylphosphonic acids as intermediate products or plant protection agents (see, for example, European Patent Application No. 14,684), as a constituent of low-flammability polymers, as an active grouping in surface-active substances and the like, it was desirable to obtain an economically advantageous access to arylphosphonic acids by means of a single-stage process, starting from readily accessible precursors.

It has been possible, surprisingly, to achieve this object by subjecting an aromatic or heterocylic compound to anodic oxidation in the presence of a trialkyl phosphite in an undivided cell.

The present invention relates, therefore, to a process for the preparation of phosphonic acid esters of the formula I

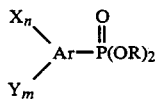 (I)

in which
Ar denotes phenyl, a binuclear or polynuclear aromatic radical, cycloheptatrienyl, furyl or pyridyl,
X denotes $(C_1-C_{18})$-alkyl and $(C_1-C_6)$-alkoxy which can be substituted by cyano, phenyl, naphthyl, benzyloxy, phenoxy, benzoxazolyloxy, benzthiazolyloxy, quinoxalinyloxy, quinolinyloxy, pyridyloxy, naphthoxy, phenylmercapto and naphthylmercapto, it being possible for these aromatic or hetero-aromatic radicals to be substituted by one to 3 radicals which represent $(C_1-C_4)$-alkyl or have the meaning of the radical Y, phenylcarbonylamino, $(C_1-C_6)$-alkylcarbonylamino, $(C_1-C_6)$-alkylmercapto, $(C_1-C_4)$-alkoxy-$(C_1-C_4)$-alkyl, $(C_1-C_4)$-alkoxycarbonylamino, $(C_1-C_4)$-alkoxycarbonyloxy, $(C_1-C_4)$-alkoxycarbonyl-$(C_1-C_4)$-alkoxy, mono-$(C_1-C_4)$-alkylaminocarbonyloxy, di-$(C_1-C_4)$-alkylaminocarbonyloxy or phenylaminocarbonyloxy or two radicals X in the ortho-position together form an aliphatic chain having 3 or 4 carbon atoms, it being possible for up to 2 non-adjacent carbon atoms to be replaced by oxygen, and for this chain to be monosubstituted or disubstituted by $(C_1-C_4)$-alkyl, in particular methyl,
Y denotes halogen, $(C_1-C_4)$-alkoxycarbonyl, $(C_1-C_4)$-alkylcarbonyl, nitro, nitroso, cyano, $(C_1-C_4)$-alkylsulfonyl, phenylsulfonyl, $(C_1-C_4)$-alkoxysulfonyl, phenoxysulfonyl, di-[$(C_1-C_4)$-alkoxy]-phosphinyl, di-[$(C_1-C_4)$-alkyl]-phosphinyl, [O-$(C_1-C_4)$-alkoxy-O-$(C_1-C_4)$-alkyl]-phosphinyl or $(C_1-C_4)$-alkyl which is substituted by 1 to 6 halogen atoms, in particular $CF_3$, formyl or amidosulfonyl which can be substituted in the amino radical by 1 to 2 $(C_1-C_4)$-alkyl radicals or by a phenyl radical,
R denotes $(C_1-C_6)$-alkyl,
n denotes 1, 2 or 3 and
m denotes 0, 1, 2 or 3, m being preferably smaller than n, which comprises subjecting a compound of the formula II

to anodic oxidation in an undivided electrolytic cell in the presence of a compound of the formula III $P(OR)_3$ (III)

and of a $(C_1-C_4)$-alkanol, the radicals $X_n$, $Y_m$, Ar and R having the meanings mentioned above.

The radicals R, X and Y in the above formulae can have identical or different meanings.

Some of the compounds of the formula I are new.

The invention also relates, therefore, to new compounds of the abovementioned formula I in which Ar denotes phenyl, X denotes phenoxy, benzoxazolyloxy, benzthiazolyloxy, quinoxalinyloxy, quinolinyloxy or pyridyloxy, it being possible for these radicals to be substituted by 1 to 3 radicals belonging to the group comprising chlorine, nitro, $CF_3$, mono-$(C_1-C_4)$-alkylaminocarbonyloxy or di$(C_1-C_4)$-alkylaminocarbonyloxy, $(C_1-C_4)$-alkylcarbonylamino, $(C_1-C_4)$-alkyl, $(C_1-C_4)$-alkoxy, $(C_1-C_4)$-alkylcarbonyloxy or $(C_1-C_4)$-alkoxycarbonyl-$(C_1-C_4)$-alkoxy or two radicals X in the ortho-position together form an aliphatic chain having 3 or 4 carbon atoms, it being possible for one or two non-adjacent carbon atoms to be replaced by oxygen and for this chain to be monosubstituted or disubstituted by $(C_1-C_4)$-alkyl, Y denotes $(C_1-C_4)$-alkoxycarbonyl, R denotes $(C_1-C_4)$-alkyl, n denotes 1, 2 or 3 and m denotes 0 or 1.

These compounds are valuable intermediate stages for the preparation of plant protection agents (European Patent Application No. 14,684).A In the present process, the $(C_1-C_4)$-alkanol has the function of a solvent and a reagent, since it reacts with the phosphorus component of the formula III by taking up a radical —OR and, in some cases, with an exchange of the alkoxy radicals.

It is preferable to use methanol or ethanol.

It was surprising that the alcoholic solvent does not attack the compound of the formula II during the electrolysis, although, for example, methoxylation reactions of aromatic compounds under similar conditions have been described (F. Beck, Elektroorganische Chemie ("Electroorganic Chemistry"), Verlag Chemie GmbH, Weinheim/Bergstrasse 1974 and N. L. Weinberg, Technique of Electroorganic Synthesis, Part I, J. Wiley & Sons, New York, 1974). The trialkylphosphite is capable, surprisingly, of holding its own against the competition of the nucleophilic solvent for the aromatic compound.

The use of $(C_1-C_4)$-alkanols as the solvent compared with acetonitrile as the solvent, as described in the publications JCS Perkin I 1979, 2,023 and Chem. Pharm. Bull. 27, 1,271 (1979) is extremely advantageous, since it permits an electrolyte of good conductivity to be made up.

In contrast with the publications JCS Perkin I 1979, 2,023 and Chem. Pharm. Bull. 27, 1,271 (1979), the process according to the invention operates under homogeneous conditions, since the protons formed intermediately at the anode do not have to be bound by a base; on the contrary, they are removed from the electrolyte system in the form of gaseous hydrogen by being discharged at the cathode.

The process according to the invention operates advantageously under conditions of constant current and can therefore also be carried out in industrial electrolytic cells, in contrast with JCS Perkin I 1979, 2,023 and Chem. Pharm. Bull. 27, 1,271 (1979), which describe a procedure at constant potential.

The concentration of the aromatic starting compound of the formula II can be varied within the range from 1 to about 40% by weight, relative to the total electrolyte. It is preferably between 15 and 25% by weight.

It is advantageous to carry out the reaction using a trialkyl phosphite of the formula III in which the radicals R are identical with the alkyl radical of the alkanol (solvent), since otherwise mixed arylphosphonic acid esters are obtained by transesterification reactions with the solvent.

The concentration of trialkyl phosphite of the formula III should be approximately equimolar in comparison with the amount of aromatic component. In addition, an excess or a deficiency of trialkyl phosphite is not harmful for the process. It is preferable to employ the reactants in an equimolar ratio and to meter in the trialkyl phosphite subsequently during the electrolysis, as required.

As well as the $(C_1-C_4)$-alkanol, further inert solvents, such as, for example, acetonitrile, methylene chloride, acetone and ether, can also be added, if desired, as a solvent.

The solid electrolyte used is, for example, the conducting salts which are customary in electrochemistry. Any salts which are readily soluble in the solvent used and which are stable under the experimental conditions are suitable. Essentially, these alkali metal salts or onium salts of the acids HF, $HBF_4$, $HPF_6$, $HClO_4$, $H_2SO_4$, $H_3PO_4$ or toluenesulfonic acid. Preferred salts are tetramethylammonium methylsulfate, potassium fluoride and tetramethylammonium dimethylphosphate.

The concentration of the conducting salts is appropriately within the range from about 0.01 to 20% by weight, but is preferably within the limits from about 0.1 to 5% by weight, relative to the total electrolyte.

The choice of electrode material is not critical. Any electrode materials which are stable under the conditions of electrolysis can be employed in the process according to the invention. These are, for example, graphite, graphite-filled plastics, platinum, vitreous carbon and titanium electrodes coated with noble metals. The cathodes used are preferably materials having a low hydrogen overvoltage. It is also possible, however, to use graphite.

The anode current densities can be varied widely, between 5 and 500 $mA/cm^2$, preferably between 50 and 200 $mA/cm^2$ and especially between about 50 and 100 $mA/cm^2$.

The current conversion should advantageously be about 2 Faradays per mole of the compound II. In principle, however, lower and higher current conversions are also possible, depending on whether partial conversion or as quantitative a conversion as possible is desired.

The temperature of electrolysis is generally between 0° C. and the boiling point of the electrolyte mixture. A temperature range between 30° and 45° C. is preferred.

The material discharged from the electrolysis is worked up in a known manner. Solvents and any starting material which may still be present can be recovered by distillation and recycled to the electrolysis. The conducting salt can also be re-used for a subsequent batch.

The following examples serve to illustrate the invention.

EXAMPLE 1

Preparation of dimethyl 2,5-dimethoxyphenylphosphonate (a) Apparatus: an undivided, thermostatically controlled glass pot cell having a volume of approx. 300 ml, an internal thermometer, a reflux condenser and a magnetic stirrer.

Anode: a platinum gauze cylinder
Cathode: a platinum gauze cylinder
Temperature: 30°–32° C.
Anode current density: 17.3 $mA/cm^2$
Quantity of electricity: 5.6 Ah
Electrolyte:
  13.8 g (0.1 mole) of hydroquinone dimethyl ether
  12.4 g of trimethyl phosphite
  7.0 g of $Me_4N^+MeSO_4^-$
  200 ml of MeOH The electrolyte is concentrated at a pressure of 200 mm Hg, water is added to the residue, and the mixture is extracted with methylene chloride. After the organic phase has been dried, the solvent is removed by distillation and the residue is fractionated under an oil pump vacuum.

22.35 g of dimethyl 2,5-dimethoxyphenylphosphonate are obtained. This corresponds to a material yield of 91% and a current efficiency of 87%.

(b) Apparatus: as described under Example 1
Anode: platinum gauze cylinder
Cathode: platinum gauze cylinder
Temperature: 30°–35° C.
Anode current density: 17.0 $mA/cm^2$
Quantity of electricity: 4.15 Ah
Electrolyte:
  13.8 g of hydroquinone dimethyl ether
  16.6 g of triethyl phosphite 7.0 g of Me$_4$N$^+$MeSO$_4^-$
200 ml of ethanol After electrolysis, the crude electrolyte has the following composition in % by area, according to gas chromatography[1]: 11.8% of triethyl phosphite, 16.5% of educt and 56.4% of diethyl 2,5-dimethoxyphenylphosphonate. After working up in aqueous phase followed by distillation, 3.62 g of hydroquinone dimethyl ether and 14.95 g of diethyl 2,5-dimethoxyphenylphosphonate are obtained. This gives a yield of 74%, while the current efficiency is 71%.

[1] % by area = area under peak as % of total area under curve (c) Apparatus: A mono-pole, undivided, continuous-flow cell, electrode distance approx. 1 mm, electrolyte circulated by pumping during electrolysis
Anode: graphite
Cathode: stainless steel
Temperature: 26° C.
Anode current density: 25 mA/cm$^2$
Quantity of electricity: 70 Ah
Electrolyte:
    165.6 g (1.2 moles) of hydroquinone dimethyl ether
    148.8 g of trimethyl phosphite
    60 g of Me$_4$N$^+$MeSO$_4^-$
    2,400 ml of methanol When electrolysis is complete, the crude electrolyte contains 2.3% by area of educt and 80.4% by area of dimethyl 2,5-dimethoxyphenylphosphonate.

The methanol is distilled off on a rotary evaporator and the conducting salt is then precipitated and reisolated from the residue by adding methylene chloride. Fractional distillation of the organic phase gives 212.6 g of product, which corresponds to a yield of 72% and a current efficiency of 66%.

EXAMPLE 2

Preparation of dimethyl 3,4-dimethoxyphenylphosphonate

Apparatus: as described under Example 1
Anode: platinum gauze cylinder
Cathode: platinum gauze cylinder
Temperature: 34° C.
Anode current density: 19 mA/cm$^2$
Quantity of electricity: 8.64 Ah
Electrolyte:
    13.8 g (0.1 mole) of dimethyl pyrocatecholate
    16.4 g of trimethyl phosphite
    7.0 g of Me$_4$N$^+$MeSO$_4^-$
    200 ml of methanol The product is isolated by distilling off the methanol, extracting the residue with methylene chloride/water, drying the organic phase and then concentrating the latter again. Fracional distillation gives 20.68 g (85%) of dimethyl 3,4-dimethoxyphenylphosphonate, at a current efficiency of 52%.

EXAMPLE 3

Preparation of dimethyl 2,4-dimethoxyphenylphosphonate (a) Apparatus: as described under Example 1
Anode: platinum gauze cylinder
Cathode: platinum gauze cylinder
Temperature: 33°–40° C.
Anode current density: 19 mA/cm$^2$
Quantity of electricity: 8.55 Ah
Electrolyte:
    13.8 g (0.1 mole) of resorcinol dimethyl ether
    16.2 g of trimethyl phosphite
    7.0 g of Me$_4$N$^+$MeSO$_4^-$
    200 ml of methanol Working up as under Example 4. Fractional distillation gives 20.15 g (82%) of dimethyl 2,4-dimethoxyphenylphosphonate, at a current efficiency of 51%.

(b) Apparatus: as described under Example 1
Anode: platinum gauze cylinder
Cathode: platinum gauze cylinder
Temperature: 33°–37° C.
Anode current density: 19 mA/cm$^2$
Quantity of electricity: 8.39 Ah
Electrolyte:
    13.8 g (0.1 mole) of resorcinol dimethyl ether
    15.1 g of trimethyl phosphite
    5.0 g of KF
    200 ml of methanol Working up is carried out analogously to Example 4. Distillation gives 19.17 g (78%) of methyl 2,4-dimethoxyphenylphosphonate, which corresponds to a current efficiency of 50%.

EXAMPLE 4

Preparation of dimethyl 2-methoxyphenylphosphonate and 4-methoxyphenylphosphonate Apparatus: as described under Example 1
Anode: platinum gauze cylinder
Cathode: platinum gauze cylinder
Temperature: 33°–37° C.
Anode current density: 19 mA/cm$^2$
Quantity of electricity: 5.82 Ah
Electrolyte:
    10.8 g (0.1 mole) of anisole
    15.4 g of trimethyl phosphite
    7.0 g of Me$_4$N$^+$MeSO$_4^-$
    200 ml of MeOH When electrolysis is complete, the crude electrolyte contains 2.2% by area of educt and two isomeric products: dimethyl 2-methoxyphenylphosphonate (41.0% by area) and dimethyl 4-methoxyphenylphosphonate (25.9% by area).

Working up analogously to Example 4 gives 13.98 g of distillate containing the ortho-isomer and the paraisomer in a ratio of 56:44. The total yield is accordingly 65%, at a current efficiency of 60%.

EXAMPLE 5

Preparation of dimethyl naphthalene-1-phosphonate and naphthalene-2-phosphonate

Apparatus: as described under Example 1
Anode: platinum gauze cylinder
Cathode: platinum gauze cylinder
Temperature: 25°–30° C.
Anode current density: 19 mA/cm$^2$
Quantity of electricity: 7.3 Ah
Electrolyte:
    12.8 g (0.1 mole) of naphthalene
    20.4 g of trimethyl phosphite
    7.0 g of Me$_4$N$^+$SO$_4^-$
    200 ml of methanol Working up is carried out analogously to Example 4 and gives, in addition to 3.3 g of naphthalene, 14.2 g (81%) of a mixture of isomers, dimethylnaphthalene-1- phosphonate (88.8% by area) and dimethylnaphthalene-2-phosphonate (9.7% by area). The current efficiency is 44%.

EXAMPLE 6

Preparation of dimethyl 2-methoxynaphthalene-1-phosphonate

Apparatus: as described under Example 1
Anode: platinum gauze cylinder
Cathode: platinum gauze cylinder
Temperature: 34°–39° C.
Anode current density: 19 mA/cm$^2$
Quantity of electricity: 5.52 Ah
Electrolyte:
    15.8 g (0.1 mole) of 2-methoxynaphthalene
    16.1 g of trimethyl phosphite
    7.0 g of NMe$_4$$^3$$^0$MeSO$_4$–
    200 ml of methanol The electrolyte contains, in addition to 5.8% by area of educt, 73.7% by area of dimethyl 2-methoxynaphthalene-1-phosphonate; working up analogously to Example 4 gives 19.56 g (80%) of product as well as 1.31 g of starting substance. The current efficiency is 71%.

EXAMPLE 7

Preparation of dimethyl 2-acetamidophenylphosphonate and 4-acetamidophenylphosphonate Apparatus: as described under Example 1
Anode: platinum gauze cylinder
Cathode: platinum gauze cylinder
Temperature: 25°–30° C.
Anode current density: 19 mA/cm$^2$
Quantity of electricity: 10.35 Ah
Electrolyte:
    13.5 g (0.1 mole) of acetanilide
    17.95 g of trimethyl phosphite
    7.0 g of Me$_4$N$^+$MeSO$_4$–
    200 ml of MeOH When electrolysis is complete, the methanol is distilled off in a rotary evaporator, water is added to the residue and the mixture is extracted several times with ether. The organic phase is dried and the solvent is removed. The partly crystalline residue obtained is poured onto a suction filter and filtered with suction; the crystals obtained are subsequently washed with a little acetone.

4.0 g of dimethyl 4-acetamidophenylphosphonate are obtained. The filtrate is subjected to fractional distillation, which gives a fraction of 9.35 g composed of 87% of dimethyl 2-acetamidophenylphosphonate and 13% of educt. The total yield is accordingly 55%, at a current efficiency of 26%.

EXAMPLE 8

Preparation of dimethyl biphenyl-2-phosphonate and biphenyl-4-phosphonate

Apparatus: as described under Example 1
Anode: platinum gauze cylinder
Cathode: platinum gauze cylinder
Temperature: 30°–35° C.
Anode current density: 19 mA/cm$^2$
Quantity of electricity: 8.64 Ah
Electrolyte:
    15.4 g (0.1 mole) of biphenyl
    21.4 g of trimethyl phosphite
    7.0 g of Me$_4$N$^+$MeSO$_4$–

After electrolysis, the crude electrolyte contains 3.5% of educt, 27.6% of dimethyl biphenyl-2-phosphonate and 32% of dimethyl biphenyl-4-phosphonate (in % by area), and is worked up analogously to Example 4. Distillation gives 1.25 g of biphenyl and 19.44 g (81%) of a mixture of the products. The current efficiency is 46%.

EXAMPLE 9

Preparation of dimethyl 2-methoxy-5-chlorophenylphosphonic acid

Apparatus: as described under Example 1
Anode: vitreous carbon
Cathode: stainless steel
Temperature: 30°–35° C.
Anode current density: 36.4 mA/cm$^2$
Quantity of electricity: 6.95 Ah
Electrolyte:
    14.3 g (0.1 mole) of 4-chloroanisole
    23.7 g of trimethyl phosphite
    5.0 g of Me$_4$N$^+$MeSO$_4$–
    200 ml of methanol The material discharged from the electrolyte contains 1.9% of educt, 2.6% of dimethyl 2-chloro-5-methoxyphenylphosphonate and 45.9% of dimethyl 2-methoxy-5-chlorophenylphosphonate (in % by area). Working up analogously to Example 4 gives 18.42 g (74%) of a mixture of products, at a current efficiency of 57%.

EXAMPLE 10

Preparation of dimethyl 2-phenoxyphenylphosphonate and 4-phenoxyphenylphosphonate Apparatus: as described under Example 1
Anode: platinum gauze cylinder
Cathode: platinum gauze cylinder
Temperature: 31°–34° C.
Anode current density: 19 mA/cm$^2$
Quantity of electricity: 6.55 Ah
Electrolyte:
    17.0 g (0.1 mole) of diphenyl ether
    18.9 g of trimethyl phosphite
    7.0 g of Me$_4$N$^+$MeSO$_4$–
    200 ml of methanol When electrolysis is discontinued, the electrolyte contains 4.1% of educt, 32.6% of dimethyl 2-phenoxyphenylphosphonate and 42.7% of dimethyl 4-phenoxyphenylphosphonate. Working up analogously to Example 4 gives 18.55 g (67%) of a mixture of isomers (o/p=44/56). The current efficiency is 55%.

EXAMPLE 11

Preparation of dimethyl 5-carbomethoxy-2-methoxyphenylphosphonate and 2-carbomethoxy-5-methoxyphenylphosphonate Apparatus: as described under Example 1
Anode: platinum gauze cylinder
Cathode: platinum gauze cylinder
Temperature: 30°–40° C.
Anode current density: 19 mA/cm$^2$
Quantity of electricity: 7.52 Ah
Electrolyte:

16.6 g (0.1 mole) methyl 4-methoxybenzoate
16.3 g of trimethyl phosphite
7.0 g of Me$_4$N$^+$MeSO$_4^-$
200 ml of methanol When electrolysis is complete, the solvent is distilled off on a rotary evaporator, water is added to the residue and the mixture is extracted with ether several times. The organic phase is dried and the ether is removed. This leaves 7.2 g of crystalline starting material. Extracting the aqueous phase with methylene chloride and subsequently working up the extract by distillation gives 12.2 g (79%) of a mixture of products composed of 83% by area of dimethyl 5-carbomethoxy-2-methoxyphenylphosphonate and 17% by area of dimethyl 2-carbomethoxy-5-methoxyphenylphosphonate. The current efficiency is 32%.

EXAMPLE 12

Preparation of dimethyl 2-p-tolyloxy-5-methylphenylphosphonate and 5-p-tolyloxy-2-methylphenylphosphonate Apparatus: as described under Example 1
Anode: platinum gauze cylinder
Cathode: platinum gauze cylinder
Temperature: 32°–37° C.
Anode current density: 19 mA/cm$^2$
Quantity of electricity: 9.30 Ah
Electrolyte:
 19.8 g (0.1 mole) ditolyl ether
 25.5 g of trimethyl phosphite
 5.0 g of Me$_4$N$_+$MeSO$_4^-$ Working up is carried out analogously to Example 4. Distillation in a bulb tube oven gives 20.55 g (67%) of a mixture of isomers composed of 3 parts of dimethyl 2-p-tolyloxy-5-methylphenylphosphonate and 1 part of dimethyl 2-methyl-5-p-tolyloxyphenylphosphonate. The current efficiency is 39%.

EXAMPLE 13

Preparation of dimethyl 2,5-dimethoxy-4-dimethylphosphonatophenylphosphonate

Apparatus: as described under Example 1
Anode: platinum gauze cylinder
Cathode: platnium gauze cylinder
Temperature: 35°–37° C.
Anode current density: 19 mA/cm$^2$
Quantity of electricity: 7.79 Ah
Electrolyte:
 12.3 g (0.05 mole) of dimethyl 2,5-dimethoxyphenylphosphonate
 16.9 g of trimethyl phosphite
 7.0 g of Me$_4$N$^+$MeSO$_4^-$
 200 ml of methanol When electrolysis is complete, the crude electrolyte is concentrated on a rotary evaporator, water is then added to the residue and the mixture is extracted several times with methylene chloride. After the organic phase has been dried over anhydrous sodium sulfate, the solvent is substantially removed and isopropyl ether is added to the residue. This gives a crystalline precipitate of 5.4 g (31%) of dimethyl 2,5-dimethoxy-4-dimethylphosphonatophenylphosphonate. The current efficiency is 11%.

EXAMPLE 14

Preparation of dimethyl 2-tert.-butoxy-5-methylphenylphosphonate and 5-tert.-butoxy-2-methylphenylphosphonate Apparatus: as described under Example 1
Anode: platinum gauze cylinder
Cathode: platinum gauze cylinder
Temperature: 25°–31° C.
Anode current density: 19 mA/cm$^2$
Quantity of electricity: 8.36 Ah
Electrolyte:
 16.4 g (0.1 mole) of p-cresyl tert.-butyl ether
 20.5 g of trimethyl phosphite
 7.0 g of Me$_4$N$^+$MeSO$_4^-$
 200 ml of methanol When electrolysis is complete, working up is carried out as described under Example 4. This gives 15.8 g (58%) of a mixture of products composed of 4 parts of dimethyl 2-tert.-butoxy-5-methylphenylphosphonate and 1 part of dimethyl 2-methyl-5-tert.-butoxyphenylphosphonate. The current efficiency is 37%.

EXAMPLE 15

Preparation of dimethyl 2-methoxy-5-methylphenylphosphonate and 5-methoxy-2-methylphenylphosphonate Apparatus: as described under Example 1
Anode: platinum gauze cylinder
Cathode: platinum gauze cylinder
Temperature: 31°–32° C.
Anode current density: 19 mA/cm$^2$
Quantity of electricity: 4.71 Ah
Electrolyte:
 12.2 g (0.1 mole) of 4-methylanisole
 15.2 g of trimethyl phosphite
 7.0 g of Me$_4$N$^+$MeSO$_4^-$
 200 ml of methanol When electrolysis is complete, the procedure is the same as that described under Example 4. Working up the crude electrolyte, which, as well as 11.8% by area of starting material, contains 56.1% by area of dimethyl 2-methoxy-5-methylphenylphosphonate and 11.5% by area of dimethyl 2-methyl-5-methoxyphenylphosphonate, gives 16.31 g of a mixture of products composed of the two isomers. 1.9 g of starting material are also isolated from the process, so that the material yield amounts to 84% and the current yield to 80%.

EXAMPLE 16

Preparation of dimethyl 5-acetyl-2-methoxyphenylphosphonate

Apparatus: as described under Example 1
Anode: platinum gauze cylinder
Cathode: platinum gauze cylinder
Temperature: 30°–35° C.
Anode current density: 19 mA/cm$^2$
Quantity of electricity: 7.09 Ah
Electrolyte:
 15.0 g (0.1 mole) of 4-methoxyacetophenone
 20.1 g of trimethyl phosphite
 7.0 g of Me$_4$N$^+$MeSO$_4^-$
 200 ml of methanol Working up when electrolysis is complete is carried out analogously to the description under Example 4. 4.05 g of starting material are recovered by distillation. 2.95 g (16%) of dimethyl 2-methoxy-5-acetylphenylphosphonate are crystallized from the high-boiling fraction (163°–185° C./0.03 mm) by means of $CH_2Cl_2$/isopropyl ether. The current efficiency is 8.8%.

EXAMPLE 17

Preparation of dimethyl furan-2-phosphonate

Apparatus: as described under Example 1
Anode: platinum gauze cylinder
Cathode: platinum gauze cylinder
Temperature: 28°–32° C.
Anode current density: 17.0 mA/cm$^2$
Quantity of electricity: 17.0 Ah
Electrolyte:
   20.4 g (0.3 mole) of furan
   50.0 g of trimethyl phosphite
   7.0 g of $NMe_4^+MeSO_4^-$
   180 ml of methanol When electrolysis is complete, the crude electrolyte contains 7.5% by area of 2,5-dimethoxy-2,5-dihydrofuran and 0.9% by area of dimethyl furan-2-phosphonate. Working up is carried out as described under Example 4; the recovery of furan and trimethyl phosphite was dispensed with. 4.15 g of dimethyl furan-2-phosphonate (7.5% current efficiency) are obtained by distillation.

EXAMPLE 18

Preparation of 2'-diethylphosphonyl-4'-methoxybenzanilide

Apparatus: an undivided, thermostatically controlled glass pot cell having a volume of approx. 300 ml, an internal thermometer, a reflux condenser and a magnetic stirrer.
Anode: platinum gauze cylinder
Cathode: platinum gauze cylinder
Temperature: 30°–35° C.
Anode current density: 14 mA/cm$^2$
Quantity of electricity: 2.44 Ah
Electrolyte:
   5.65 g (0.025 mole) of 4'-methoxybenzanilide
   5 g of $Me_4N^+MeSO_4^-$
   22 g of triethyl phosphite
   150 ml of ethanol
   50 ml of acetone When electrolysis is complete, the solvent is distilled off, the residue is taken up in acetone and the conducting salt is filtered off. The filtrate is concentrated again and freed from readily volatile constituents in an oilpump vacuum. Incipient distillation in a bulb tube oven leaves an oily residue, which is chromatographed over neutral aluminum oxide in a 1:1 mixture of petroleum ether (60°–90° C.)/isopropyl ether. 5.06 g of 2'-diethylphosphonyl-4'-methoxybenzanilide are obtained. This corresponds to a material yield of 56% and a current efficiency of 31%.

EXAMPLE 19

Preparation of dimethyl 2-acetamidonaphthalene-1-phosphonate

Apparatus: as described under Example 1a
Anode: platinum gauze cylinder
Cathode: platinum gauze cylinder
Temperature: 24°–25° C.
Anode current density: 24 mA/cm$^2$
Quantity of electricity: 6.17 Ah
Electrolyte:
   17.0 g of N-2-naphthylacetamide
   29.2 g of trimethyl phosphite
   7.6 g of $Me_4N^+MeSO_4^-$ When electrolysis is complete, the mixture is worked up with the aid of water and the crude product is incipiently distilled under an oilpump vacuum. The residue (24.5 g, crystallined) corresponds to a crude yield of 91%. 17.92 g of product are obtained by chromatography over $SiO_2$ in acetone (material yield 66.5%; current efficiency 53.1%).

EXAMPLE 20

Preparation of 3-dimethoxyphosphoryl-4-acetamidobenzenesulfonamide

Apparatus: as described under Example 1a
Anode: platinum gauze cylinder
Cathode: platinum gauze cylinder
Temperature: 30°–35° C.
Anode current density: 17–24 mA/cm$^2$
Quantity of electricity: 8.16 Ah
Electrolyte:
   10.7 g of 4-acetamidobenzenesulfonamide
   22 g of trimethyl phosphite
   6 g of $Me_4N^+MeSO_4^-$ When electrolysis has been discontinued, the solvent is distilled off, the residue is extracted by shaking with methylene chloride/water, and the organic phase is dried over sodium sulfate. The drying agent and the methylene chloride are removed, the residue is subjected to incipient distillation under an oilpump vacuum and a 1:1 mixture of i-propyl ether/acetonitrile is added. 4 g of crystalline product are isolated, as well as a further 2.4 g of product obtained by chromatography over $SiO_2$ using acetonitrile/i-propyl ether. Material yield 48.3%; current efficiency 13%.

EXAMPLE 21

Preparation of dimethyl 2,4,6-trimethylbenzenephosphonate

Apparatus: as described under Example 1c
Anode: graphite
Cathode: stainless steel
Temperature: 20°–23° C.
Anode current density: 35 mA/cm$^2$–15 mA/cm$^2$
Quantity of electricity: 126 Ah
Electrolyte:
   240 g of mesitylene
   354 g of trimethyl phosphite
   50 g of $Me_4N^+MeSO_4^-$
   2500 ml of MeOH After electrolysis, the electrolyte contains 15.8% by area of product and also 26.1% by area of mesitylene and 13.1% by area of trimethyl phosphite. The crude electrolyte is worked up by being concentrated on a rotary evaporator. The conducting salt is precipitated from the residue by means of ethyl acetate and is recovered by filtration. Fractional distillation gives 141 g of dimethyl 2,4,6-trimethylbenzenephosphonate, corresponding to a material yield of 31% and a current efficiency of 26%.

EXAMPLE 22

Preparation of dimethyl 2-acetamido-5-chlorobenzenephosphonate

Apparatus: as described under Example 1c
Anode: graphite
Cathode: stainless steel
Temperature: 30°-32° C.
Anode current density: 30-6 mA/cm$^2$
Quantity of electricity: 199 Ah
Electrolyte:
  191 g of 4-chloroacetanilide
  316 g of trimethyl phosphite
  51 g of Me$_4$N$^+$MeSO$_4^-$
  2500 ml of MeOH The crude electrolyte is worked up by being concentrated, and the residue is then subjected to incipient distillation under an oilpump vacuum up to a head temperature of 75° C. 1.5 l of ethyl acetate are added to the crystallizing residue, and the mixture is heated on a steambath; the conducting salt which has been thrown out of solution is then removed by filtration and the filtrate is concentrated. This gives a mash of crystals (187 g) from which 150 g of dimethyl 2-acetamido-5-chlorobenzenephosphonate are isolated by column chromatography. This corresponds to a material yield of 48% at a current efficiency of 15%.

EXAMPLE 23

Preparation of dimethyl 2,4,6-cycloheptatrienephosphonate

Apparatus: as described under Example 1a
Anode: platinum gauze cylinder
Cathode: platinum gauze cylinder
Temperature: 26°-30° C.
Anode current density: 23 mA/cm$^2$
Quantity of electricity: 10.89 Ah
Electrolyte:
  18.4 g of cycloheptatriene
  30.4 g of trimethyl phosphite
  5.0 g of Me$_4$N$^+$MeSO$_4^-$
  200 ml of MeOH The mixture is worked up by distilling off the solvent and then working up the residue with the aid of water. Distillation at 0.3 mbar gives 22.9 g of dimethyl 2,4,6-cycloheptatrienephosphonate. (Material yield: 57%; current efficiency: 55%).

EXAMPLE 24

Preparation of fluorene phosphonic acid esters

Apparatus: as described under Example 1a
Anode: platinum gauze cylinder
Cathode: platinum gauze cylinder
Temperature: 30°-35° C.
Anode current density: 23 mA/cm$^2$
Quantity of electricity: 24.58 Ah
Electrolyte:
  24.9 g of fluorene
  33.3 g of trimethyl phosphite
  5.0 g of Me$_4$N$^+$MeSO$_4^-$
  170 ml of MeOH
  30 ml of methylene chloride After the electrolysis, the electrolyte is concentrated and worked up with the aid of water. Distillation in a bulb tube oven gives 23.5 g of a mixture of two isomeric dimethyl fluorenephosphonates, probably a mixture of dimethyl fluorene-2-phosphonate and dimethyl fluorene-4-phosphonate in a ratio of 66:34 (material yield 68.3%; current efficiency 18.6%).

EXAMPLE 25

Preparation of dimethyl 4-benzyloxynaphthalene-1-phosphonate

Apparatus: as described under Example 1a
Anode: platinum gauze cylinder
Cathode: platinum gauze cylinder
Temperature: 34°-36° C.
Anode current density: 23 mA/cm$^2$
Quantity of electricity: 5.84 Ah
Electrolyte:
  23.4 g of 1-naphthyl benzyl ether
  15.4 g of trimethyl phosphite
  7.0 g of Me$_4$N$^+$MeSO$_4^-$
  200 ml of MeOH When the current has been switched off, the electrolyte is concentrated and worked up with the aid of water. The crude product obtained is recrystallized from isopropyl ether. This gives 22.2 g of product at a material yield of 65% and a current efficiency of 60%.

EXAMPLE 26

Preparation of 2,3,5,6-tetramethylbenzenephosphonate

Apparatus: as described under Example 1a
Anode: platinum gauze cylinder
Cathode: platinum gauze cylinder
Anode current density: 17.5 mA/cm$^2$
Quantity of electricity: 10.4 Ah
Electrolyte:
  13.4 g of durene
  28.6 g of trimethyl phosphite
  5.0 g of Me$_4$N$^+$MeSO$_4^-$
  200 ml of MeOH When the electrolysis has been discontinued, the electrolyte contains 56% by area of dimethyl 2,3,5,6-tetramethylbenzenephosphonate as well as 29% by area of durene.

EXAMPLES 27-34

The phosphonic acid esters indicated in the table were prepared as described under Example 1, using the appropriate starting compounds. The compounds were isolated in the form of oils by distillation in a bulb tube oven or by chromatography.

Resulting compounds of the formula I in which Ar is phenyl and the phosphonic acid radical occupies position 1 on the phenyl ring:

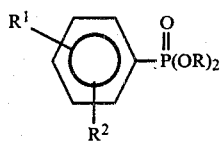
| Example No. | R¹ | R² | R | Ratio of isomers | Total yield |
|---|---|---|---|---|---|
| 27 | 4-[CF₃—C₆H₃—O—] | 2-(CH₃O—) | CH₃ | 53/47 | 81% |
|  | 2-[CF₃—C₆H₃—O—] | 4-(CH₃O—) | CH₃ |  |  |
| 28 | 2-BzO— | 5-[Cl—C₆H₃—O—] | CH₃ | / | 31% |
|  | 5-BzO— | 2-[Cl—C₆H₃—O—] |  |  |  |
| 29 | 2-BzO— | 5-[CF₃—C₆H₂(Cl)—O—] | CH₃ | — | 65% |
| 30 | 2-[CH₃CO₂CCH(CH₃)O—] | 5-[Cl—C₆H₂(Cl)—O—] | CH₃ | 80/20 | 68% |
|  | 5-[CH₃CO₂CCH(CH₃)O—] | 2-[Cl—C₆H₂(Cl)—O—] | CH₃ |  |  |
| 31 | 2-[CH₃CO₂CCH(CH₃)O—] | 5-[CF₃—C₆H₃—O] | CH₃ | 75/25 | 68% |
|  | 5-[CH₃CO₂CCH(CH₃)O—] | 2-[CF₃—C₆H₃—O] | CH₃ |  |  |
| 32 | 2-(6-Cl—Benzoxazol-2-yl) | 5-[EtO₂CCH(CH₃)O—] | C₂H₅ | 4/1 | 65% |
|  | 5-(6-Cl—Benzoxazol-2-yl) | 2-[EtO₂CCH(CH₃)O—] | C₂H₅ |  |  |
| 33 | 2[NC—CH₂O] | 5-Cl | CH₃ | 86/14 | 56% |
|  | 5-[NC—CH₂O] | 2-Cl | CH₃ |  |  |

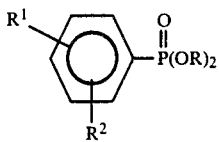

| Example No. | R¹ | R² | R | Ratio of isomers | Total yield |
|---|---|---|---|---|---|
| 34 | 2-BzO— | 4-[CF₃—⟨○⟩(Cl)—O—] | CH₃ | — | 70% |
|  | 4-BzO— | 2-[CF₃—⟨○⟩(Cl)—O—] | CH₃ |  |  |

Bz = Benzyl
Et = Ethyl

EXAMPLE 35

Preparation of 2,3-dihydro-2,2-dimethyl-5-dimethoxyphosphoryl-7-methylaminocarbonyloxybenzofuran 0.1 mole of carbofuran (2,3-dihydro-2,2-dimethyl-7-methylaminocarbonyloxybenzofuran) were reacted with trimethylphosphite analogously to Example 1a. The product was obtained in the form of an oil in a yield of 26%.

COMPARISON EXAMPLE

Preparation of 2'-diethylphosphonyl-4'-methoxybenzanilide

2'-Diethylphosphonyl-4'-methoxybenzanilide was obtained in a yield of only 38% by the process of H. Ohmoni et al., Chem. Pharm. Bull. 27, 1271 (1979), Example b, starting from triethyl phosphite and 4'-methoxybenzanilide in acetonitrile as solvent.

What is claimed is:

1. A process for the preparation of phosphonic acid esters of formula I

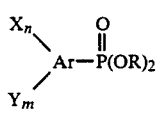

(I)

in which Ar is phenyl, a binuclear or polynuclear aromatic radical, cycloheptatrienyl, furyl or pyridyl;

X is $(C_1-C_{18})$-alkyl or $(C_1-C_6)$-alkoxy which is unsubstituted or substituted by cyano, phenyl, naphthyl, benzyloxy, phenoxy, benzoxazolyloxy, benzthiazolyloxy, quinoxalinyloxy, quinolinyloxy, pyridyloxy, naphthoxy, phenylmercapto and naphthylmercapto, wherein the aromatic or heteroaromatic radicals are unsubstituted or substituted by one to three Y substituents, $(C_1-C_4)$-alkyl, phenylcarbonylamino, $(C_1-C_6)$-alkylcarbonylamino, $(C_1-C_6)$-alkylmercapto, $(C_1-C_4)$-alkoxy-$(C_1-C_4)$-alkyl, $(C_1-C_4)$-alkoxycarbonylamino, $(C_1-C_4)$-alkoxycarbonyloxy, $(C_1-C_4)$-alkoxycarbonyl-$(C_1-C_4)$-alkoxy, mono-$(C_1-C_4)$-alkylaminocarbonyloxy, di-$(C_1-C_4)$-alkylaminocarbonyloxy or phenylaminocarbonyloxy, or two X radicals, ortho to each other, which form a ring having three or four carbon atoms, in which two non-adjacent carbon atoms can be replaced by oxygen, and in which said ring is unsubstituted, monosubstituted or disubstituted by $(C_1-C_4)$-alkyl;

Y is halogen, $(C_1-C_4)$-alkoxycarbonyl, $(C_1-C_4)$-alkylcarbonyl, nitro, nitroso, cyano, $(C_1-C_4)$-alkylsulfonyl, phenylsulfonyl, $(C_1-C_4)$-alkoxysulfonyl, phenoxysulfonyl, di-[$(C_1-C_4)$-alkoxy]-phosphinyl, di-[$(C_1-C_4)$-alkyl]-phosphinyl, [O-$(C_1-C_4)$-alkoxy-O-$(C_1-C_4)$-alkyl]-phosphinyl or $(C_1-C_4)$-alkyl which is substituted by one to six halogen atoms, formyl or amidosulfonyl which is unsubstituted or substituted in the amino radical by one to two $(C_1-C_4)$-alkyl radicals or by a phenyl radical;

R is $(C_1-C_6)$-alkyl;

n is 1, 2 or 3; and m is 0, 1, 2 or 3, which comprises subjecting a compound of the formula II $$X_n—Ar—Y_m$$ (II)

to anodic oxidation in an undivided electrolytic cell in the presence of a compound of the formula III $$P(OR)_3$$ (III)

and a $(C_1-C_4)$-alkanol.

2. The process as claimed in claim 1, wherein the $(C_1-C_4)$-alkanol employed is methanol or ethanol.

3. The process as claimed in claim 1, wherein the alkyl radical of the alkanol has the same definition R in the compound of the formula III.

4. The process as claimed in claim 1, wherein the compound of the formula I is present in a concentration of 1 to 40% by weight, relative to the total electrolyte.

5. The process as claimed in claim 1, wherein, in addition to the alkanol, further inert solvents are also added.

* * * * *